United States Patent [19]
Byram et al.

[11] Patent Number: 6,018,931
[45] Date of Patent: Feb. 1, 2000

[54] METHOD AND SUPPORT FOR SUPPORTING PACKAGES ONLY AT THEIR EDGES DURING STEAM STERILIZATION

[75] Inventors: David Clarence Byram, Palm Coast; Gregory Scott Duncan; Marlaine Gail Mills, both of Jacksonville; James Malcolm Peck, Jacksonville, all of Fla.; Kenneth Kurt Pricer, Flemington, N.J.

[73] Assignee: Johnson & Johnson Vision Products, Inc., Jacksonville, Fla.

[21] Appl. No.: 09/149,362

[22] Filed: Sep. 8, 1998

[51] Int. Cl.[7] ...................................................... B65B 55/02
[52] U.S. Cl. .......................... 53/425; 53/167; 211/126.1; 422/297; 422/302
[58] Field of Search ............................. 53/127, 167, 425, 53/426, 440; 211/126.1; 422/297, 300, 302

[56] References Cited

U.S. PATENT DOCUMENTS

| | | |
|---|---|---|
| 3,481,688 | 12/1969 | Craig et al. . |
| 3,897,818 | 8/1975 | Champel . |
| 3,971,629 | 7/1976 | Buix et al. . |
| 4,115,280 | 9/1978 | Pratt, Jr. . |
| 4,242,852 | 1/1981 | Orliaguet et al. . |
| 4,671,943 | 6/1987 | Wahlquist . |
| 4,782,942 | 11/1988 | Ashley et al. . |
| 4,986,414 | 1/1991 | Ashley et al. . |
| 5,033,252 | 7/1991 | Carter . |
| 5,284,632 | 2/1994 | Kudia et al. . |
| 5,384,103 | 1/1995 | Miller . |
| 5,424,046 | 6/1995 | Smith et al. . |
| 5,488,815 | 2/1996 | Abrams et al. . |
| 5,577,367 | 11/1996 | Abrams et al. . |
| 5,605,260 | 2/1997 | Coll . |
| 5,618,492 | 4/1997 | Auten et al. . |
| 5,628,970 | 5/1997 | Basile et al. . |
| 5,720,930 | 2/1998 | Bean . |

Primary Examiner—Daniel B. Moon

[57] ABSTRACT

A method and a support for supporting a package in a steam sterilizer, featuring support members configured and positioned to support only at least a portion of at least two opposed side edges, but not a side face, of the package. A diamond shape is particularly preferred for the support members as, when rotated at an angle, its facets provide line contact with appropriate side edges of the package.

18 Claims, 3 Drawing Sheets

METHOD AND SUPPORT FOR SUPPORTING PACKAGES ONLY AT THEIR EDGES DURING STEAM STERILIZATION

FIELD OF THE INVENTION

This invention relates to support apparatus and methods for holding packages in a steam sterilizer, particularly so as to prevent non-uniform discoloration of the package.

BACKGROUND OF THE INVENTION

A variety of objects are sterilized in package form in a steam sterilizer. One example is a package of containers of contact lenses shown, for example in U.S. Pat Nos. 5,488,815 and 5,577,367. That is, a plurality of such containers are packaged, and the entire package is placed in a steam sterilizer. The package is preferably already labeled, such as by laser ablation or any other method.

The problem is that, typically, the heat of the sterilization causes discoloration of the exposed side faces of the package. If such packages are supported by sitting on their bottom side faces, then all but the bottom becomes discolored, which leaves a non-uniform appearance. This suggests to the customer that there is something wrong with the package. Therefore, there has been a need, prior to the invention, to provide a method and apparatus for supporting the package so that the discoloration appears uniform because it attacks substantially all of all the side faces of the package uniformly.

SUMMARY OF THE INVENTION

The above-noted problem is solved by supporting the package(s) in the steam sterilizer only along certain of the side edges defined as the intersection of two adjacent side faces.

More specifically, in accordance with one aspect of the invention, there is provided a method of preventing uneven discoloration of a package in a steam sterilizer, said package having a plurality of side faces each forming, with an adjacent side face, a side edge of intersection, some of said side edges being opposed. The method comprises the steps of:

a) providing in a steam sterilizer a supporting tray comprising package-supporting members, said members having surfaces configured to contact only at least a portion of at least two of said opposed side edges and not a side face of side package; and b) placing a package to be steam-sterilized, in the sterilizer so that it contacts said supporting members only along at least said portions of said two opposed side edges;

so that any heat of steam sterilization subsequently applied has uniform access to substantially all of the surface area of all of said side faces.

In accordance with another aspect of the invention, there is provided a tray for supporting a package in a steam sterilizer for uniform exposure of said package to discoloration by heat, said package having a plurality of side faces each forming, with an adjacent side face, a side edge of intersection, some of side edges being opposed. The tray comprises sufficient package-supporting members to support a package in a steam sterilizer, said members comprising surfaces configured and positioned to contact only at least a portion of at least two of said opposed side edges and not a side face of said package.

In accord with yet another embodiment of the invention, there is provided a tray for supporting a package in a steam sterilizer for uniform exposure of said package to discoloration by heat, said package having a plurality of side faces each forming, with an adjacent side face, a side edge of intersection, some of side edges being opposed. The tray comprises sufficient package-supporting members to support a package in a steam sterilizer, said members including means for contacting and supporting the package only at at least a portion of at least two of said opposed side edges and not a side face of said package.

Accordingly, it is an advantageous feature of the invention that packages are steam-sterilized so that any heat or steam discoloration occurs uniformly over substantially all of all of the side faces, including the bottom side face.

It is a related advantageous feature of the invention that support for such packages during steam sterilization occurs only along certain side edges and not on a side face.

Other advantageous features will become apparent upon reference to the following Detailed Description, when read in light of the attached drawings.

DESCRIPTION OF THE PREFERRED EMBODIMENTS

The invention is described in connection with certain preferred embodiments, in which the package being steam-sterilized or autoclaved is a six-side-faced paper-based carton with rectangular sides intersecting to form twelve side edges, is packaged with containers of contact lenses, the containers being preferably labeled on the outside by a label prepared by laser ablation, such as by the techniques described in commonly-owned U.S. application Ser. No. 09/112,186, filed on Jul. 9, 1998 (Attorney Docket No. VTN408). In addition, the invention can be used with packages of any material and any number of side faces, containing any article or articles, the package being labeled by any technique, including laser ablation and thermal printing, or not labeled at all prior to steam-sterilization. Still further, any form of steam-sterilization, conventional or otherwise, can be applied to a package supported by this invention.

As noted above, the invention resides in a method and a tray that support the package so as to expose to the heat of the steam sterilization, substantially all the surface area of all the side faces of the package, thereby achieving uniform discoloration, if any.

Figure 1:
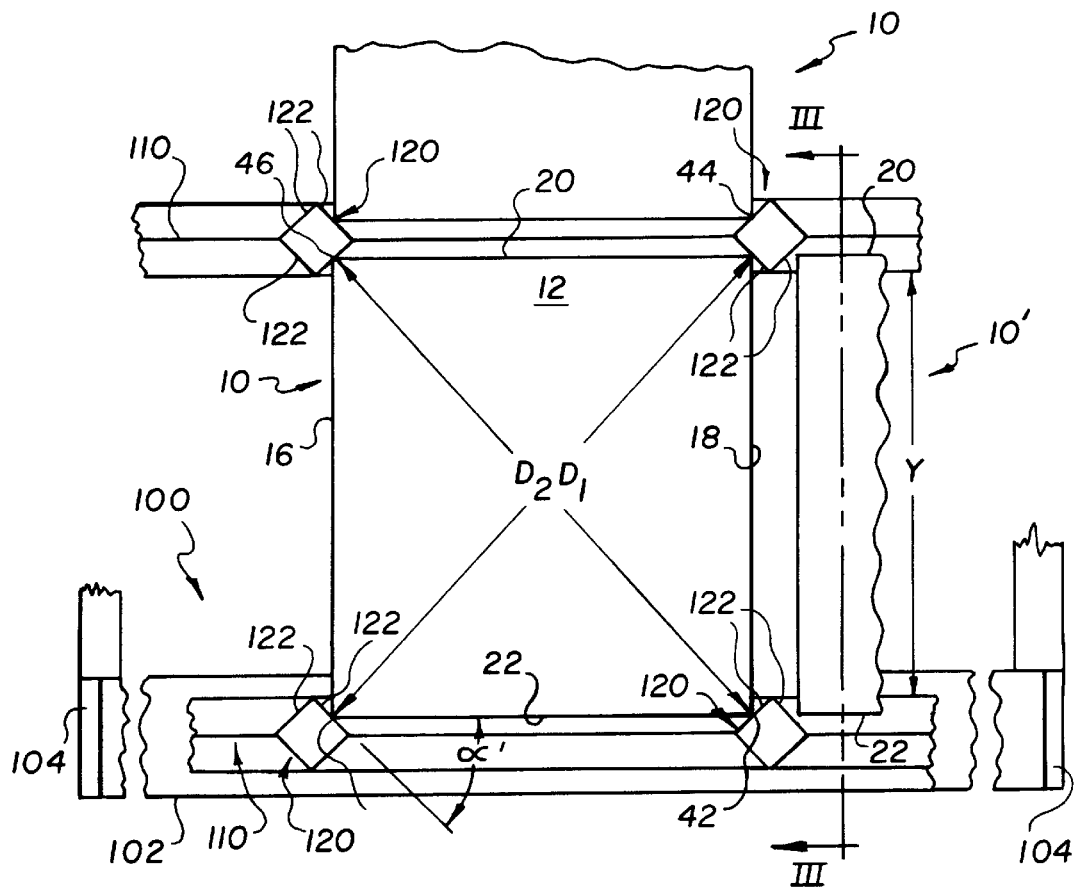
FIG. 1 is a fragmentary plan view of a plurality of packages on their support as positioned in a steam sterilizer.
Figure 2:
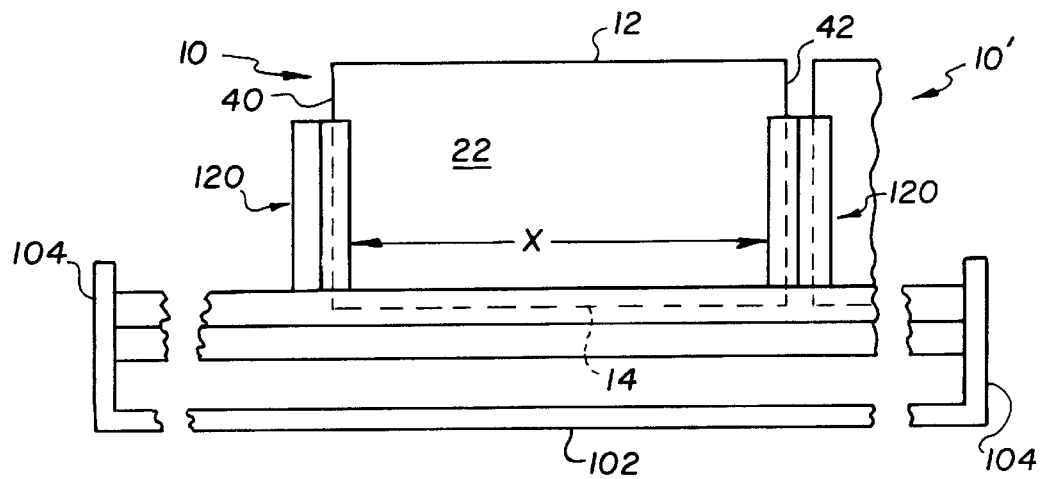
FIG. 2 is a fragmentary side elevational view of the arrangement shown in FIG. 1.
Figure 3:
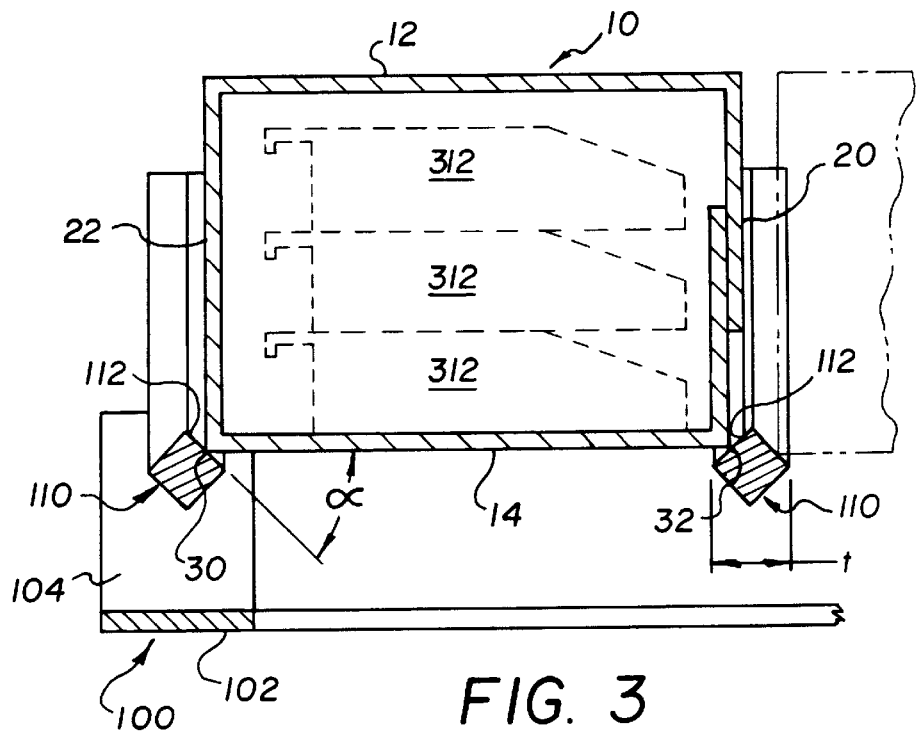
FIG. 3 is a sectional view taken generally along the line III—III of FIG. 1.

More specifically, FIGS. 1 and 2, each package 10 to be steam-sterilized comprises six side faces 12, 14, 16, 18, 20, and 22, and any two adjacent side faces of these intersect at a total of twelve side edges, of which side edges 30 and 32, FIG. 3, are bottom side edges formed by the intersections of side faces 14 and 22, and 14 and 20, respectively.

Figure 5:
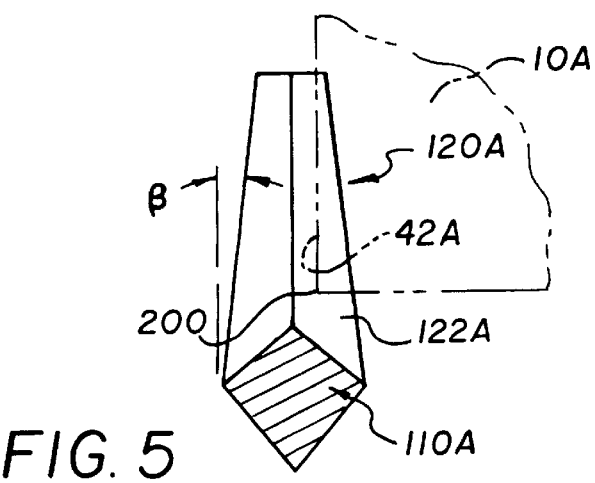
FIG. 5 is a section view taken generally along the line V—V of FIG. 4.

Additionally, side edges 46, 42 and 44, 46 are opposing corner side edges, FIG. 5, formed by their respective side faces.

In accordance with the invention, the method of preventing uneven discoloration resides in supporting the package only along at least a portion of at least two opposed side edges, such as the bottom side edges 30 and 32, FIG. 3.

To that end, a tray support 100 is provided within the steam sterilizer (not shown because it is conventional). It comprises a frame base 102, shoulders 104 extending vertically from base 102, and package support members 110 extending horizontally between shoulders 104, spaced apart horizontally a distance "Y", FIG. 1. Distance "Y" is selected to ensure that a package 10 will, in fact, sit on members 110 without falling between them, when the package is positioned as shown (preferably with the longest dimension extending along distance "D", and the shortest extending vertically as shown in FIG. 2.)

Additional, vertically extending support members 120 are attached to, such as by screw threads, members 110, spaced along each member 110 a distance "X", FIG. 2, sufficient to ensure that package 10 cannot slide out horizontally between them. That is, members 120 are disposed to be generally perpendicular to members 110. Although only four members 120 are shown mounted on only two members 110, it will be appreciated that any number of members 110 can be provided on base 102 in the direction of dimension Y, and any number of members 120 in the direction of dimension X. As shown, members 120 do not extend the full height of the package. However, they may do so and even exceed the package height.

To ensure the package contacts members 110 only along bottom side edges 30, 32, or a portion thereof, members 110 are shaped, FIG. 3, preferably so as to be a diamond in transverse cross-section. Thus, members 110 have four facets, one of which (112) does the actual package contacting. This facet is turned at an angle alpha from the horizontal, again to ensure the contact is along bottom side edge 30 and not bottom side face 14. Such angle alpha is preferably approximately 45°, that is, ±15°.

Opposed members 110, so configured and positioned, are by themselves sufficient to constrain package 10 to stay in place on the support, in many cases. See, for example, package 10' located at the right side of FIG. 1. However, in some cases it is advisable to add the constraints of support members 120 at the corner side edges 40, 44 and/or 42, 46, such as in the event package 10 might shift on the support. Still further, members 120 guide the operator in positioning and holding adjacent packages (shown in FIG. 1) so that they do not contact each other. To that end, any two opposed members 120 contacting opposed corner side edges 40, 44, or 42, 46 can be in contact with the package. Also, if dimensions of the package are carefully controlled, all four package corner side edges can be in contact with and constrained by all four members 120.

Thus, members 120, like members 110, are preferably diamond in transverse cross-section, FIG. 1, having four facets 122 each of which is angled at angle alpha' to the horizontal, to ensure that only the corner side edge is contacted. Angle alpha' can be the same as or different from, angle alpha, and is also preferably approximately 45°.

Still further, if package 10 is light enough, and the diagonal dimensions "$D_1$" and "$D_2$", FIG. 1, are carefully controlled to tightly fit the package dimensions, then the four support members 120 can be the sole means for supporting and holding package 10, without the package also contacting members 110 underneath.

Figure 4:
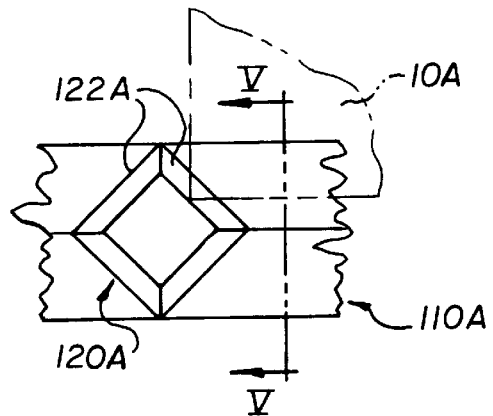
FIG. 4 is a fragmentary enlarged plan view of an alternative embodiment of the package supporting members; the package outline being shown in phantom.

It is not essential that the facets 122 of vertical support members 120 be perfectly vertical, and be spaced apart to tightly fit the diagonal dimensions of package 10. Instead, FIGS. 4 and 5, the vertical support members can have its facets be tapered inwardly upwardly, to allow for package 10 to be supported at four corners, and for dimensional variations to occur in the diagonal distances $D_1$ and $D_2$. Parts similar to those previously described bear the same reference numeral, to which the distinguishing suffix "A" is appended.

Thus, the support comprises horizontal support members 110A that are diamond-shaped as before. Vertical support members 120A are provided appropriately spaced along members 110A. These also are generally diamond-shaped in transverse cross-section, except that the facets 122A thereof are tapered inwardly as the member 120A extends upwardly, at an angle beta, FIG. 5. Such angle can be between 1° and 30°. This then allows package 10A, shown in phantom, to contact facet 122A only at its four corner portions 200 formed as the intersection of the two bottom side edges and one of the corner side edges, of which only 42A is shown. That is, the taper of facets 122A will allow the package dimensions to vary and still cause corner portions 200 to sit onto the appropriate facet 122A of the four members 122A. In this fashion, only the corner portion of each of the noted opposed side edges of the package contacts the support members, since the bottom side edges are otherwise raised up away from members 110A. The taper also renders loading of the package easier than if members 120A were vertical without a taper, as in the earlier embodiment.

Still further, other transverse cross-sectional shapes are useful for members 110 and 120, besides the diamond shape. For example, FIGS. 6A and 6B, a cylinder can be used, or a triangular cross-section can be used, and still make only edge contact with package 10. Parts similar to those previously described bear the same reference numeral, to which the distinguishing suffix "B" or "C" is appended, respectively.

Figure 6A:
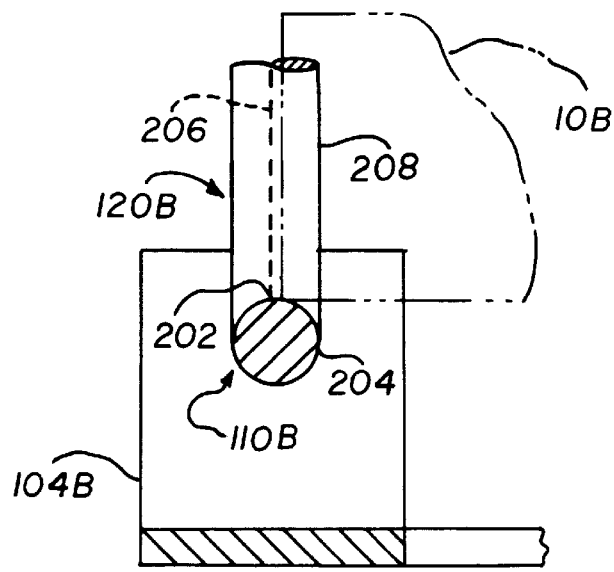
FIGS. 6A and 6B are elevational views in section similar to FIG. 3, but showing yet other alternative embodiments.

Thus, FIG. 6A, frame shoulders 104B mount horizontal support members 110B on which are mounted vertical support members 120B, as described before. However, all of members 110B and 120B are cylindrical, of a diameter that causes the package side edges to contact the member somewhere between the extreme contact lines 202 and 204 on member 110B. Similarly, package 10B contacts, if at all, with its corner side edges the vertical support members 120B somewhere between extreme contact lines 206 and 208. Care must be taken that vertical support members 120B are of sufficient diameter as to space adjacent packages sufficiently apart horizontally, as shown in FIG. 1, to prevent contact with each other.

Figure 6B:
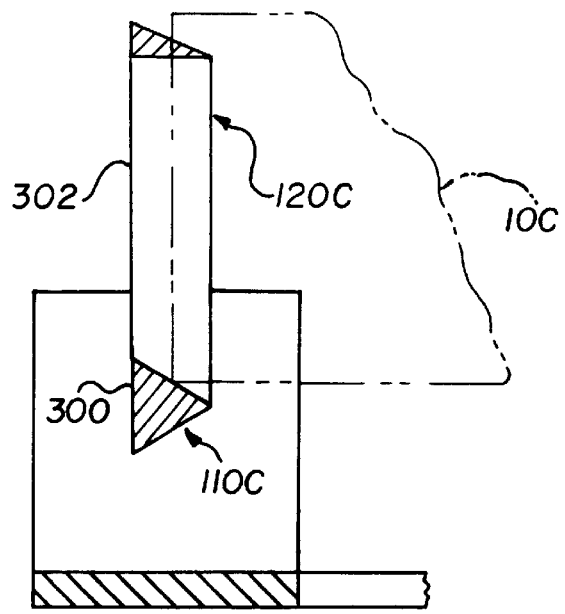

In FIG. 6B, members 110C and 120C are both triangular in transverse cross-section. Vertical facet 300 of member 110C must face away from any package 10C to be supported. Likewise, facet 302 of members 120C that parallels the side faces of package 10C, is faced away from the package(s). A drawback of such an embodiment is that it allows for only a single row of packages to be supported, rather than multiple rows as in the other embodiments.

Still further, a mixture of diamond, cylindrical, and triangular shaped supporting members can be used, as is readily apparent.

The effect of all of the above embodiments is to allow the heat of the sterilization to have access to all of the surface areas of all of the package side faces, so that any discoloration occurs uniformly thereover. To that end, the minimum spacing should be about 0.5 cm, to allow the heat uniform access. A useful example of such spacing apart of packages 10 in the horizontal directions is about 0.52 cm in the X direction and 0.82 cm in the Y direction. The corner-to-corner dimension "t", FIG. 3, of supporting member 110 that provides this is about 1.8 cm. The corresponding corner-tocorner dimension for the vertical supporting members 120 in this embodiment is about 1.3 cm.

Non-discoloration of any side edges due to their contact with supporting members is of no significance.

The kind of package that this process works best with, is that made from paper comprising solid bleached sulfate paperboard stock having a nominal thickness of about 0.41 mm, +or − 10%, filled with $TiO_2$ as a white pigmentation, at a wet laydown of less than about 10% by weight of the paper content, which is coated with a heat-resistant polymeric acrylic aqueous dispersion such as that available from Algan, Inc., under the tradename "Algloss A003-A", at a wet laydown of between about 3.9 and 5.8 grams/meter$^2$ (0.8 and 1.2 pounds per thousand sq. ft.) Such paper provides protection against wetting, heat damage, and color shifting of any printed matter due to the steam sterilization.

The sterilization of the package is effective to sterilize its contents as well, such as containers 312, FIG. 3, of contact lenses.

The invention disclosed herein may be practiced in the absence of any element which is not specifically disclosed herein.

The invention has been described in detail with particular reference to preferred embodiments thereof, but it will be understood that variations and modifications can be effected within the spirit and scope of the invention.

What is claimed is:

1. A method of preventing uneven discoloration of a package in a steam sterilizer, said package having a plurality of side faces each forming, with an adjacent side face, a side edge of intersection, some of said side edges being opposed, the method comprising the steps of:
   a) providing in a steam sterilizer a supporting tray comprising package-supporting members, said members having surfaces configured to contact only at least a portion of at least two of said opposed side edges and not a side face of side package; and
   b) placing a package to be steam-sterilized, in the sterilizer so that it contacts said supporting members only along at least said portions of said at least two opposed side edges;
   so that any heat of steam sterilization subsequently applied has uniform access to substantially all of the surface area of all of said side faces.

2. A method as defined in claim 1, wherein said package comprises six side faces, and said adjacent side faces form a total of twelve side edges of intersections of which two are opposed bottom side edges and four are opposed corner side edges; and
   wherein said surfaces are configured, and said package is placed in said step b), so as to provide contact between said package-supporting surfaces and only at least a portion of said two bottom side edges and at least a portion of at least two of said four opposed corner side edges.

3. A method as defined in claim 1 or 2, wherein said surfaces are configured in the shape of a diamond in transverse cross-section, the surfaces in contact with said package edges being disposed at an approximate 45° angle with respect to the adjacent side faces forming the side edge in contact with said contacting surface.

4. A method as defined in claims 1 or 2, wherein said surfaces are configured in the shape of a cylinder.

5. A method as defined in claim 1, wherein said supporting members contact said package at four of its corners.

6. A tray for supporting a package in a steam sterilizer for uniform exposure of said package to discoloration by heat, said package having a plurality of side faces each forming, with an adjacent side face, a side edge of intersection, some of side edges being opposed; the tray comprising:
   sufficient package-supporting members to support a package in a steam sterilizer, said members comprising surfaces configured and positioned to contact only at least a portion of at least two of said opposed side edges and not a side face of said package.

7. A tray as defined in claim 6, wherein said package comprises six side faces, and said adjacent side faces form a total of twelve side edges of intersections of which two are opposed bottom side edges and four are opposed corner side edges;
   and wherein said surfaces are configured and positioned to contact only at least a portion of said two bottom side edges and at least a portion of at least two of said four opposed corner side edges.

8. A tray as defined in claims 6 or 7, wherein said surfaces are configured in the shape of a diamond in transverse cross-section, the surfaces in contact with said package edges being disposed at an approximate 45° angle with respect to the adjacent side faces forming the side edge in contact with said contacting surface.

9. A tray as defined in claims 6 or 7, wherein said surfaces are configured in the shape of a cylinder.

10. A tray for supporting a package in a steam sterilizer for uniform exposure of said package to discoloration by heat, said package having a plurality of side faces each forming, with an adjacent side face, a side edge of intersection, some of side edges being opposed; the tray comprising:
    sufficient package-supporting members to support a package in a steam sterilizer, said members including means for contacting and supporting the package only at at least a portion of at least two of said opposed side edges and not a side face of said package.

11. A tray as defined in claim 10, wherein said package comprises six side faces, and said adjacent side faces form a total of twelve side edges of intersections of which two are opposed bottom side edges and four are opposed corner side edges;
    wherein surfaces are configured and positioned to contact only at least a portion of said two bottom side edges and at least a portion of at least two of said four opposed corner side edges;
    so that any heat-discoloration of the package is uniformly distributed over the entire package except for said two bottom side edges and said at least portions of said four opposing side edges.

12. A tray as defined in claims 10 or 11, wherein said means comprise diamond-shaped members positioned so that package-contacting surfaces thereof are disposed at an approximate 45° angle with respect to the adjacent package side faces forming the side edge in contact with said package-contacting surface.

13. A tray as defined in claims 10 or 11, wherein said means comprise individual cylindrical members.

14. A tray as defined in claim 10, wherein at least some of said supporting members are positioned to be generally perpendicular to others of said supporting members.

15. A tray as defined in claim 14, wherein some of said supporting members are positioned to be generally vertical.

16. A tray as defined in claim 15, wherein said generally vertical members are tapered upwardly inwardly, so that a package contacts said tapered members at four corners of said package.

17. A tray as defined in claim 6 or 10, and further including supported on the tray, a package comprising a paperboard coated with a polymeric acrylic dispersion.

18. A tray as defined in claim 17, wherein said paperboard further includes a white pigmentation.

* * * * *